US006208286B1

United States Patent
Rostislavovich et al.

(10) Patent No.: US 6,208,286 B1
(45) Date of Patent: Mar. 27, 2001

(54) METHOD FOR DISCOVERING THE LOCATION OF A LIVING OBJECT AND MICROWAVE LOCATION DEVICE FOR REALIZING THE SAME

(76) Inventors: Osipov Viktor Rostislavovich, kv. 36, d. 18, mkr. 1, g. Yubileiny, Moskovskaya obl., 141090 (RU); Ikramov Gairat Saidkhakimovich, kv. 108, d.16, ul. Pelshe, Olimpiiskayas, derevnya, Moscow, 117602 (RU)

(*) Notice: Subject to any disclaimer, the term of this patent is extended or adjusted under 35 U.S.C. 154(b) by 0 days.

(21) Appl. No.: 09/434,675

(22) Filed: Nov. 5, 1999

(30) Foreign Application Priority Data

May 6, 1997 (RU) .................................................. 9700140

(51) Int. Cl.[7] ...................................................... G01S 13/12
(52) U.S. Cl. ......................... 342/135; 342/118; 342/134; 342/195
(58) Field of Search ................................ 342/22, 27, 28, 342/89, 175, 192, 193–196, 61, 118, 127–145; 600/453; 340/522, 573.1, 573.4

(56) References Cited

U.S. PATENT DOCUMENTS

| 3,831,173 | 8/1974 | Lerner . | |
|---|---|---|---|
| 3,993,995 | * 11/1976 | Kaplan et al. | 342/61 |
| 4,008,469 | 2/1977 | Chapman . | |
| 4,072,942 | 2/1978 | Alongi . | |
| 4,513,748 | * 4/1985 | Nowogrodzki et al. | 600/453 |
| 4,958,638 | 9/1990 | Sharp et al. . | |
| 4,967,751 | 11/1990 | Sterzer . | |
| 5,448,501 | * 9/1995 | Hablov et al. | 340/573.1 |
| 5,530,429 | * 6/1996 | Hablov et al. | 340/552 |
| 5,790,032 | * 8/1998 | Schmidt | 340/573.4 |
| 5,867,257 | * 2/1999 | Rice et al. | 342/192 X |
| 6,031,482 | * 2/2000 | Lemaitre et al. | 342/22 |

FOREIGN PATENT DOCUMENTS

| 3137012 A1 | 3/1983 | (DE) . |
|---|---|---|
| 42 41 664 C2 | 6/1995 | (DE) . |
| 2076336 C1 | 3/1997 | (RU) . |

OTHER PUBLICATIONS

Chen, Kun–Mu, et al. An X—Band Microwave Life–Detection System, *IEEE Transactions on Biomedical Engineering*. vol. 33. No. 7(1986) pp. 697–700.

Chuang, Huey–Ru, et al. Automatic Clutter–Canceler for Microwave Life–Detection Systems, *IEEE Transactions On Instrumentation And Measurement*. vol. 40. No. 4. (1991) pp. 747–750.

* cited by examiner

Primary Examiner—Bernarr E. Gregory
(74) Attorney, Agent, or Firm—Graybeal Jackson Haley LLP (57) ABSTRACT

The method includes radiating an RF signal within a time Tt, receiving a reflected signal within a fixed time Tr equal in duration to the fixed time Tt of the radiated signal plus a delay $\tau_d$ between the end of the signal radiation and the beginning of the reflected signal reception. Once a modulated component is detected, a level of the component is measured and the reception time of the reflected signal is modified. This is carried out until the level of the modulated component decreases relative to that of the initially reflected RF signal and until the signal stops coming in. A distance is further determined from the reception time of the reflected signal with the modulated component. The method can be implemented using a microwave locator comprising a modulator and a transmitter which includes an oscillator, a power splitter and a transmitting antenna. A receiver comprises a receiving antenna, a microwave receiver, a preamplifier/demodulator and a signal processing unit. The modulator is tunable. The apparatus further includes a first pulse modulator in the transmitter and a second pulse modulator in the microwave receiver. The modulator has a control output which is connected to a control input of the second pulse modulator so that the receiver receives the reflected signal with a delay relative to the end of the signal radiation by the transmitter, and the enable time of the microwave receiver is modified. The signal processing unit measures a level of the modulated component.

16 Claims, 5 Drawing Sheets

METHOD FOR DISCOVERING THE LOCATION OF A LIVING OBJECT AND MICROWAVE LOCATION DEVICE FOR REALIZING THE SAME

FIELD OF THE INVENTION

The invention relates to search and rescue service and is useful in active sounding of obstructions formed as the result of accidents and natural disasters, to objectively detect the presence of a human with life signs, such as breath, heart beating and movements.

BACKGROUND OF THE INVENTION

Various conventional apparatuses using the action of a radio interferometer with a compensation channel for extracting a modulated component of a radio frequency (RF) signal, corresponding to the frequency of human's heart rate or breath, are known in the prior art (PCT/DE 95/00062; U.S. Pat. No. 4,967,751; DE A 4241664; IEEE Transactions on Instrumentation and Measurement, Bd.40, No.4, August 1991, New York, US, p.p.747–760, Chuang, Chen, Chen, "Automatic Clutter-Canceler for Microwave Life-Detection Systems"). The apparatuses are employed in noncontact diagnostics and also useful in detecting a living object under obstructions formed, for instance, after earthquakes, accidents or avalanches. The main constraint on the use of the conventional apparatuses for detecting alive people under obstructions is that it is impossible to select a search zone by distance, and the apparatuses are highly susceptible to the presence of an operator handling them.

A conventional electronic system for detecting a living object comprises a modulator and a transmitter including an oscillator, a power splitter and a transmitting antenna, a receiver including a receiving antenna, a microwave receiver, a preamplifier/modulator and signal processing unit, a second signal output of the power splitter being connected to a control input of the microwave receiver, and one of control outputs of the unit being connected to the control input of the microwave receiver (DE, A, 42416164).

In the above apparatus, a dc component in a reflected signal is compensated for at an input of the microwave receiver prior to amplification, this resulting in additional noise introduced by compensation means, and the modulator serves only to provide a possibility of amplification of a signal component modulated by a living object, lying outside the noise region 1/f. The apparatus, therefore, has an additional source of amplitude and phase noise at its input. This restricts a minimal level of the received signal and impairs sensitivity, prohibiting the determination of a distance to a living object with such an apparatus.

Disclosed in IEEE Transactions on BME, V.33, Jul. 7, 1986, Kun-Mu Chen, D.Misra, H.-R. Chuang "An X-band Microwave Life-Detection System" is a method for locating a living object, including the steps of radiating a radio frequency (RF) signal, receiving a return RF signal at the place of the RF signal radiation, extracting a component of the received RF signal, which is modulated in amplitude and phase corresponding to the frequency of a heart rate and/or breath of a living motionless object, and judging, on the basis of the extracted component, of detecting a living object.

The above method provides for a compensation of a microwave signal reflected from a mass of motionless objects, extraction and analysis of a variable component of the reflected signal associated with the aforementioned human life signs by comparison of the reflected signal amplitude and phase with their constant values in the radiated signal. The reason for the use of compensation is the particularity of the apparatus for implementing the method. With a microwave signal reflected from a light-tight obstruction and other highly-reflecting motionless objects available within the region of a pattern of a transmitting/receiving antenna of the apparatus, and as the result of direct penetration of a signal portion from the transmitter circuit to the receiver circuit, a high-power background signal comes to the latter, this signal having a constant amplitude and phase and being capable of leaving the linearity range of the receiver's gain. On the other hand, the RF signal reflected from a living object is twice attenuated by the obstruction at the forward passage of the radiated RF signal and the return passage of the reflected RF signal. The signals are also attenuated by a distance to a living object located behind the obstruction, this attenuation being proportional to the forth power of the distance to the object. Moreover, the power level of the desired signal modulated component carrying information of the object vital activity is smaller than that of a total signal reflected from the object by a factor of 10 to 1,000.

These circumstances require that the receiving circuit should transmit a very large dynamic range of energies of the reflected RF signal, as great as 100–150 dB. The dynamic range of the desired signal energy is generally no greater than 90 dB. Hence, it is necessary to delete all useless information of motionless objects upstream of the first amplifier in the receiver by removing the background signal. This is attained by addition of a compensating microwave circuit, at an output of which a signal approximately equal in amplitude and opposite in phase to the background signal is provided by controlling parameters of the microwave circuit. The compensating signal is combined with the signal received at the receiver input in a passive combiner. The combiner outputs a power which is approximately equal to a difference of the received and background signal powers. The performance quality of the apparatus is mainly defined by the quality of this compensation, its depth, and fluctuations in the compensation circuits and the circuits controlling its parameters.

The prior art method enables effective extraction of information associated with human's vital activity, however, its abilities in performing search and rescue works are limited. The method does not restrict the search zone by distance for locating a human, and it is very susceptible to the presence of an operator handling the apparatus. The above deficiencies are caused by radiation of a continuous microwave signal which is not modulated in time and which, being reflected, combines all information of the objects disposed both within the region of the antenna pattern from its aperture plane to a maximum detection distance, and within the region of the antenna side and back lobes when the operator is nearby.

The impossibility to restrict a search zone, i.e. to preset a minimum and maximum detection distance, results in interference from people and equipment operating at the accidence site in the immediate vicinity of the search zone, and from the operator, since the high sensitivity required for extracting a modulated component is sufficient to respond to all living objects located in air space at a considerable distance or to the operator due to availability of side and back lobes of the antenna pattern. Further, when clearing away the obstruction and recovering a living object, technical means employed may injure the living object, since the conventional method does not allow the determination of a distance to a living object.

A conventional microwave locator comprises a modulator and a transmitter including an oscillator, a power splitter and a transmitting antenna having signal inputs connected in series to signal outputs, the transmitter being adapted to radiate a RF signal with modulation, a receiver including a receiving antenna, a microwave receiver, a preamplifier/demodulator and a signal processing unit, all having signal outputs connected in series with inputs, the receiver being adapted to receive a reflected RF signal modulated by a component of human's heart rate and/or breath and extract the component at the output of the preamplifier/demodulator, a second signal output of the power splitter being connected to a control input of the microwave receiver, a first control output of the modulator being connected to the transmitter, and a second and third outputs of the modulator being connected to a first and second control inputs of the preamplifier/demodulator (U.S. Pat. No. 4,958, 638).

An advantage of this apparatus over the previously mentioned prior art is in its high sensitivity in determining parameters of the modulated component, which is provided by the absence of a high self-noise level in the microwave receiver, caused by imperfect compensation at its input, introducing additional fluctuations in amplitude and phase of the compensated amplified signal. This apparatus, however, can be employed only for noncontact diagnostics. The apparatus lacks the ability to arbitrarily select a search zone and determine a distance to a living object. Moreover, in sounding distant spatial areas by the RF signal, the apparatus has dead sensitivity zones associated with single-channel phase detection employed therein.

SUMMARY OF THE INVENTION

It is an object of the present invention to provide a method for locating a living object, wherein processing of a radiated and received RF signal enables the selection of a detection zone by distance, so that to reduce a dynamic range of the signals received and to decrease susceptibility to the presence of other living objects outside the search zone.

Another object of the invention is to provide a microwave locator comprising a transmitter, a receiver and a modulator, enabling to lock a radiated RF signal, to receive a reflected RF signal at predetermined time intervals relative to the radiated RF signal, to process the signals related to trailing edges so that to measure a level of a modulated component and a distance to a living object position, thereby improving the detection quality and noise immunity.

The above object is accomplished in a method for locating a living object, including radiating a radio frequency (RF) signal, receiving a reflected RF signal at a place of the RF signal radiation, extracting a component of the received RF signal, modulated in amplitude and phase corresponding to a heart rate and/or breath frequency of a motionless living object, judging, on the basis of the extracted component, of detecting a living object, wherein in accordance with the invention said RF signal is radiated within a fixed time Tt, said reflected RF signal is received within a fixed time Tr equal in duration to the fixed time Tt of the radiated RF signal plus a delay $\tau_d$ between an end of the signal radiation and a beginning of the reflected signal reception, the method further including the steps of measuring, when a modulated component is detected, a level of the modulated component, modifying the reception time Tr of the reflected RF signal until the modulated component level decreases relative to the level of the modulated component in the reflected RF signal received within the fixed time Tt, and up to an end of arrival of the reflected RF signal, determining a distance to a living object position by the following expression:

$$D=c(\tau_d+Trr)/2$$

where c is a velocity of propagation of an RF signal, $\tau_d$ is a duration of a delay between the end of radiation and the beginning of reception of the RF signal, and Trr is a time of reception of the reflected RF signal, within which the modulated component level has been decreased, said time corresponding to an interval from the beginning of the reflected RF signal reception to the end of arrival of the reflected RF signal.

In further embodiments of the method, it can be advantageous that:

the reflected RF signal reception time is reduced in equal intervals, the reflected RF signal reception time is modified using a successive approximation technique, the RF signal is transmitted at a frequency determined as $$f(GHz)=15[0.23-\alpha d+\sqrt{(0.23-ad)^{2+0.1}}]$$

where $\alpha=tg\ \delta\sqrt{\in}$ is an attenuation ratio, $tg\delta$ and $\in$ being a dielectric loss tangent and an effective portion of a relative dielectric constant of an obstruction, respectively, at a frequency of 1 GHz, and d is an assumed maximum obstruction thickness, [m].

The above object is also attained in a microwave locator comprising a modulator, a transmitter including an oscillator, a power splitter and a transmitting antenna, all having signal inputs connected in series to signal outputs, said transmitter being adapted to radiate an RF signal with modulation, a receiver including a receiving antenna, a microwave receiver, a preamplifier/demodulator and a signal processing unit, all having signal outputs connected in series to signal inputs, said receiver being adapted to receive a reflected RF signal modulated by a living object heart rate and/or breath component, and to extract the component at an output of the preamplifier/demodulator, a second signal output of the power splitter being connected to a control input of the microwave receiver, a first control output of the modulator being connected to the transmitter, and a second and third outputs of the modulator being connected to a first and a second control inputs of the preamplifier/demodulator, wherein in accordance with the invention said modulator is tunable to modify a duration of control pulses and to lock them, said microwave locator further comprising a first pulse modulator in the transmitter and a second pulse modulator in the microwave receiver, a first signal output of the power splitter being connected to an input of the transmitting antenna via a signal input and a signal output of the first pulse modulator, and a second signal output of the power splitter being connected to a control input of the microwave receiver through a signal input and a signal output of a second pulse modulator, a control input of the first pulse modulator being connected to a first control output of the modulator to lock the radiation time of the RF signal, the modulator having a forth control output connected to a control input of the second pulse modulator to receive the reflected RF signal in the receiver with a delay relative to the end of the RF signal radiation by the transmitter and to modify an enable time of the microwave receiver, the signal processing unit being adapted to measure a modulated component level.

Further embodiments of the apparatus will be disclosed in the description of the best embodiment of the invention.

The object of the present invention is achieved owing to locking-on the RF signal radiation time to the reflected RF signal reception time with a delay $\tau_d$ between the end of the radiation and the beginning of the reception, measuring a modulated component level and determining the reflected RF signal reception time Trr within which the level of the modulated component has been decreased, said time Trr corresponding to a period from the beginning of the reflected RF signal reception to the end of arrival thereof.

Said advantages and features of the present invention will become more evident from the following description of the best embodiments of the invention with references to the accompanying drawings.

DETAILED DESCRIPTION OF PREFERRED EMBODIMENT

Figure 1:
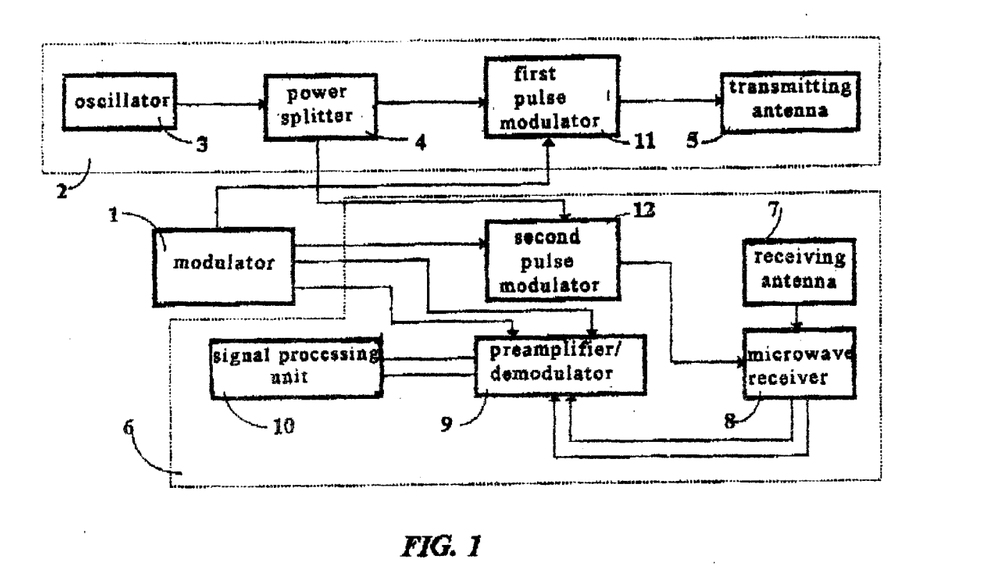
FIG. 1 is a functional block diagram of a microwave locator for implementing a method in accordance with the invention.
Figure 2:
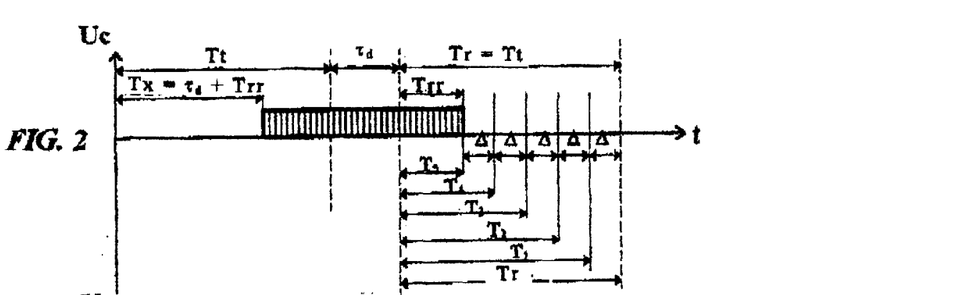
FIG. 2 is a timing diagram illustrating a method in accordance with the present invention in the case when the reflected RF signal reception time is reduced.
Figure 3:
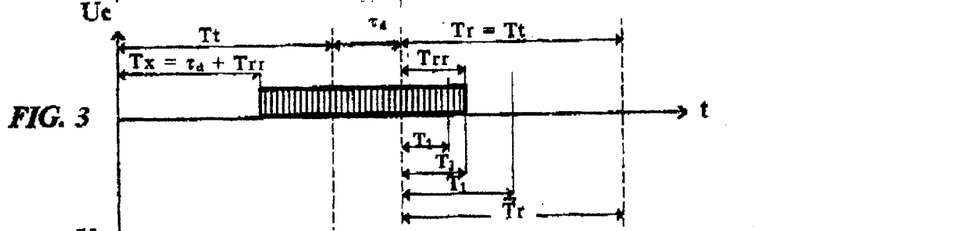
FIG. 3 is the same as FIG. 2, for the case when the reception time is modified by a successive approximation technique, with the reflected signal portion occupying a smaller part of the reception region.
Figure 4:
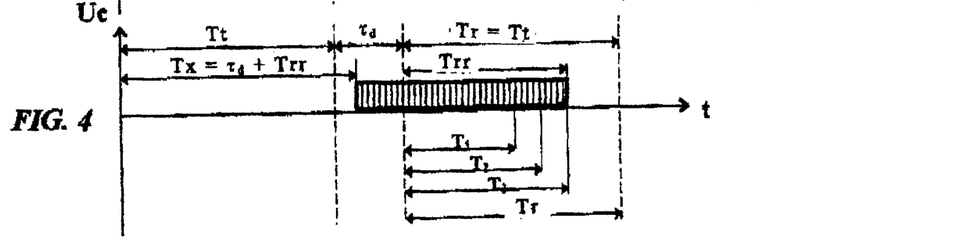
FIG. 4 is the same as FIG. 3, for the case when the reflected signal portion occupies a greater part of the reception region.

A method in accordance with the present invention can be implemented in an apparatus (FIG. 1) whose operation will be explained below with reference to timing diagrams (FIGS. 2, 3, 4). A transmitter 2 radiates an RF microwave signal within a radiation time Tt owing to timing the signal in a modulator 1 and a first pulse modulator 11. A microwave receiver 8 is enabled with a delay $\tau_{d1}$ after a time $\tau_d$ from the beginning of the RF signal radiation, owing to its timing by the modulator 1 and a second pulse modulator 12. Since, in reality, an obstruction has a restricted length, the radiation time Tt can be easily determined from the equation Tt=2 $(D_{max}+D_{min})/c$, where $D_{max}$, $D_{min}$ are a far and near search boundaries, respectively, c is a velocity of propagation of radio waves in the environment. A delay time is selected equal to $\tau_d=2D_{min}/c$.

A reflected RF signal is received in the microwave receiver 8 within a time Tr which is equal to the time Tt, as the result of its enabling for this time by the second pulse modulator 12. With such Tt, Tr and $\tau_d$, a portion of the arrived combined reflected RF signal is truncated by the microwave receiver 8, since it is enabled for the time Tr (in FIGS. 2, 3, 4, the RF signal reflected from a living object is shown by vertical hatching).

When a modulated component is detected as the result of processing the RF signal in a receiver 6, a preamplifier/demodulator 9 and a signal processing unit 10, a distance to a living object can be easily determined by a time Tx of a delay in arrival of the reflected RF signal relative to the radiated signal. However, since a front portion of the arrived signal is cut off, this delay can be determined by trailing edges of the radiated and reflected signals. To this end, a time Trr of reception of the reflected RF signal is determined, within which a modulated component level has been decreased, this time Trr corresponding to an interval from the beginning of the reflected RF signal reception to the end of the reflected RF signal arrival (FIGS. 2–4).

The time Trr can be measured by various methods depending on the algorithm of the accepted processing of modification in the time of enabling the microwave receiver 6. The reflected RF signal reception time Tr may be reduced in equal periods Δ (FIG. 2) until the modulated component level in the received signal decreases. Then, $Tx=\tau_d+T_5=\tau_d+Trr$; distance $D=c\ Tx/2\equiv c(\tau_d+Trr)/2$. However, to provide a fair accuracy, in this case the discreteness Δ should be selected reasonably small within the accuracy range of the trailing edge measurement, which is quite a long procedure, and although it simplifies the processing algorithm, the speed of determining a distance by the apparatus reduces.

To increase the speed of determining the distance D, it would be advantageous to modify the reflected RF signal reception time Tr by a successive approximation technique (FIGS. 3, 4). When a modulated component is detected, the reception time Tr is reduced by half (FIG. 3) and the modulated component level is measured at a time $T_1$. If the modulated component levels for Tr and $T_1$ are the same, the time $T_1$ is reduced by half, $T_2=T_1/2$. When the frequency component level decreases, the reception time is increased $T_3=(T_1+T_2)/2$. The procedure of halving the time when the modulated component levels are equal, and increasing the time, when the modulated component level decreases, by combining the time period corresponding to a constant modulated component level in the last period with the time period corresponding to a decreased modulated component level, and halving the obtained sum, is carried out until a required accuracy is attained. In practice, it is sufficient to carry out five to seven measurements to determine the time Trr corresponding, within the measurement error, to a distance D of up to one meter, this fully observing the requirements of search and rescue operations and permitting to recover a person uninjured from an obstruction.

The above procedure is also carried out when a modulated reflected signal is received from a far detection zone (FIG. 4). $T_1=Tr/2$. When the modulated component level decreases, $T_2=(T_1+Tr)/2$. If the modulated component level is again less that the preceding level, then $T_3=(Tr+T_2)/2$, and so on. Consequently, the method in accordance with the invention essentially consists in continuously monitoring a modulated component level for different distances $D_i$, where i is a measurement step, and determining just that value of the distance D, which corresponds to a boundary between the decrease in the modulated component level and its constant value.

To carry out such measurements, a modulated component level should be determined with a high degree of accuracy. As evidenced by numerous experiments, the modulated component extraction quality depends not only on the quality of a receiver, its intrinsic noise level, identity of the local oscillator channel to the radiated RF signal, sensitivity, etc., but also on a frequency of the radiated RF signal. Thus, at different radiation frequencies of antennas with equal efficient surfaces, different values of the extracted modulated component level can be obtained for the same object of sounding, depending on the obstruction properties. As the result, a relationship has been approximated which enables the extraction of those signal frequencies at which the modulated component level takes maximum values, using antennas with equal efficient surfaces.

$$f(GHz)=15[0.23-\alpha d+\sqrt{(0.23-ad)^2+0.1}]$$

where $\alpha=tg\,\delta\sqrt{\in}$ is an attenuation ratio, $tg\delta$ and $\in$ being a dielectric loss tangent and an effective portion of a relative dielectric constant of an obstruction, respectively, at a frequency of 1 GHz, and d is an assumed maximum obstruction thickness, [m].

By way of example, for an obstruction formed of reinforced concrete structures at d=2 m, the best radiation frequency f is 0.7 GHz, while for a brick wall at d=0.5 m, the best frequency f is about 6.2 GHz at any distance to the object detected in free space.

To operate at a frequency corresponding to a maximum detection efficiency, the apparatus can have broadband paths of the transmitter 2 and the receiver 6, a frequency-switched or frequency-tunable oscillator 3 and interchangeable transmitting and receiving antennas 5, 7 for different frequency ranges. The operating frequency is selected as a function of the obstruction thickness and electrical characteristics in accordance with the aforementioned empirical dependence derived by the inventors.

To implement the method in accordance with the invention, a microwave locator (FIG. 1) comprises a modulator 1 and a transmitter 2. The transmitter 2 includes, connected in series, an oscillator 3, a power splitter 4 and a transmitting antenna 5. The transmitter 2 is adapted to radiate an RF signal with a modulation provided by the modulator 1. A receiver 6 includes, connected in series, a receiving antenna 7, a microwave receiver 8, a preamplifier/demodulator 9 and a signal processing unit 10. A second signal output of the power splitter 4 is connected to a control input of the microwave receiver 8, a first control output of the modulator 1 is connected to the transmitter 2, while a second and third outputs of the modulator 1 are connected to a first and second control inputs of the preamplifier/demodulator 9, respectively.

The modulator 1 is tunable so that to modify a duration of control pulses and to lock them. The apparatus further includes a first pulse modulator 11 and a second pulse modulator 12. A first signal output of the power splitter 4 is connected to an input of the transmitting antenna 5 via the first pulse modulator 11, and a second signal output of the power splitter 4 is connected to the control input of the microwave receiver 8 via the second pulse modulator 12. A control input of the first pulse modulator 11 is connected to a first control output of the modulator 1 to lock the time of RF signal radiation. The modulator 1 has a forth control output connected to a control input of a second pulse modulator 12 to receive a reflected RF signal in the receiver 6 with a delay relative to the end of the RF signal radiation by the transmitter 2 and to modify the enable time of the microwave receiver 8. The signal processing unit 10 measures a level of the modulated component.

To eliminate dead sensitivity zones in the receiver 6, the use may be made of a two-channel quadrature phase detection as depicted in FIG. 1 by two links from the microwave receiver 8 via the preamplifier/demodulator 9 to the signal processing unit 10.

In technical implementation of the apparatus (FIG. 1), some conventional units may be employed, however, owing to the addition of new functional elements, new relations are provided between functional components. The transmitter 2 can further include a power amplifier 13 (FIG. 5), an output of the pulse modulator 11 being connected to an input of the transmitting antenna 5 via the power amplifier 13.

Figure 6:
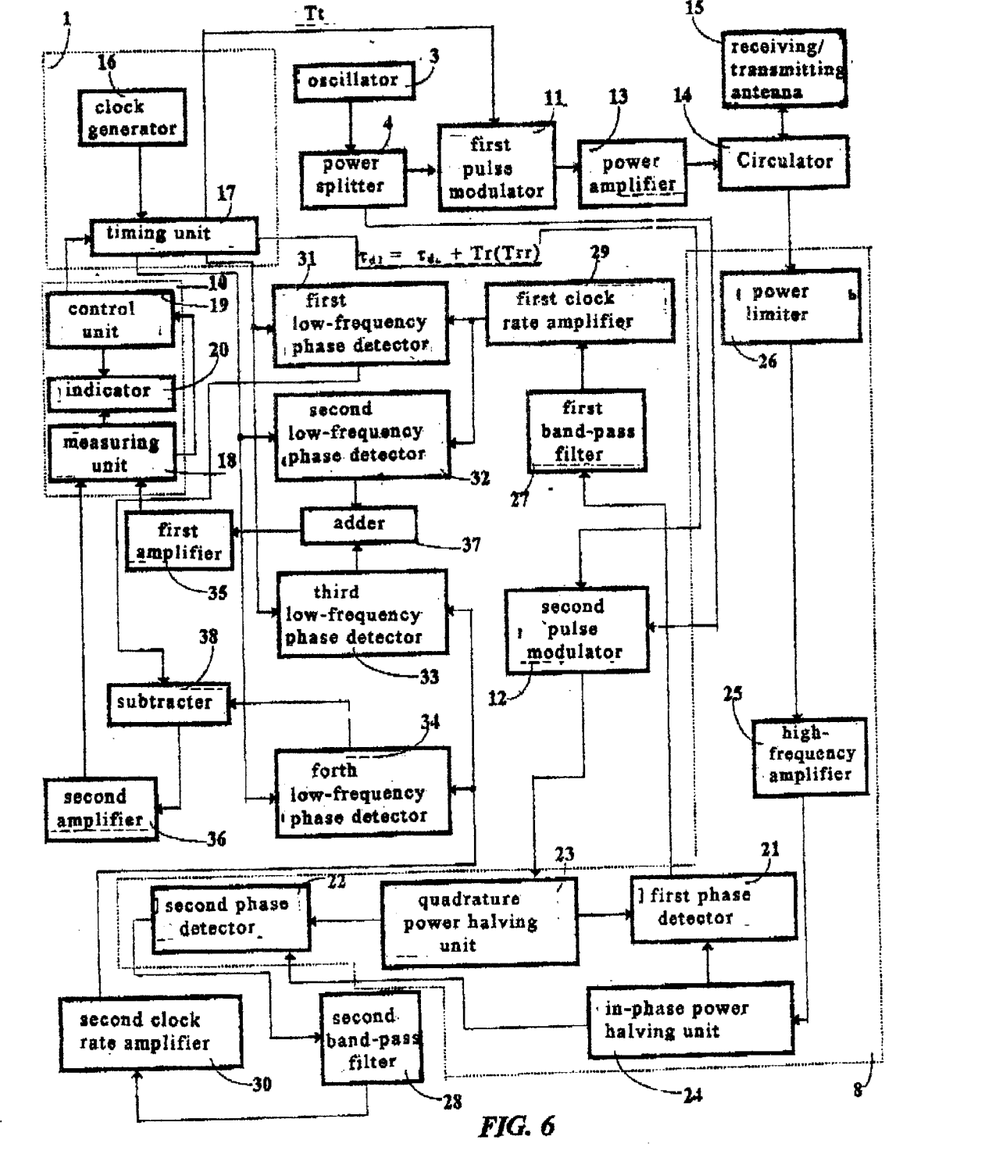
FIG. 6 is the same as FIG. 5 for another embodiment with a single transmitting/receiving antenna.

A circulator 14 (FIG. 6) can be further added, with the transmitting antenna 5 and the receiving antenna 7 (FIG. 1) being made as a single receiving/transmitting antenna 15 (FIG. 6). The first pulse modulator 11 is connected to the receiving/transmitting antenna 15 via a first branch and a second branch of the circulator 14 in the circulation direction, while the microwave receiver 8 is coupled to the receiving/transmitting antenna 15 via the second and a third branch of the circulator 14.

The modulator 1 (FIGS. 5,6) is comprised of a clock generator 16 and a timing unit 16 having a clock input connected to an output of the clock generator 16. Outputs of the timing unit 17 are first, second, third and forth outputs of the modulator 1, respectively (FIG. 1). The signal processing unit 10 is comprised of a measurement unit 18, a control unit 19 and an indicator 20. An input of the measurement unit 18 is an input of the signal processing unit 10, an information control output of the measurement unit 18 is connected to an input of the control unit 19, and a signal output is connected to a signal input of the indicator 20. A first control output of the control unit 19 is connected to a control input of the timing unit 17, while a second control output of the control unit 19 is connected to a control input of the indicator 20. The control unit 19 performs all of the functions required for switching separate units and specifying parameters to modify the reception time Tr according to a selected algorithm depending on the modulated component level measured in the measurement unit 18. As a consequence, the control unit 19 is directly connected to the control input of the timing unit 17.

To provide a two-channel quadrature phase detection, the microwave receiver 8 (FIG. 5, 6) comprises a first and second phase detector 21, 22, a quadrature power halving unit 23, an in-phase power halving unit 24 having a signal input connected to an output of the receiving antenna 7 or the receiving/transmitting antenna 15 via the circulator 14. A first output of the in-phase power halving unit 24 is connected to a first input of the first phase detector 21, while a second output thereof is connected to a first input of the second phase detector 22. An output of the second pulse modulator 12 is connected to an input of the quadrature halving unit 23, this input being the control input of the microwave receiver 8. A first output of the quadrature halving unit 23 is coupled to a second input of the first phase detector 21, while a second output thereof is connected to a second input of the second phase detector 22.

The microwave receiver 8 (FIG. 5, 6) can further include a high-frequency amplifier 25, a signal input of the in-phase halving unit 24 being coupled to an output of the receiving antenna 7 via the amplifier 25. The amplifier 25 can be a conventional low-noise amplifier.

The microwave receiver 8 (FIG. 6) can further include a power limiter 26, a signal input of the high-frequency amplifier 25 being connected to an output of the receiving antenna 7 or the receiving/transmitting antenna 15 via the power limiter 26.

In the case when high radiated power values are required to provide a detection at a great distance, it is advantageous to use the embodiment with the receiving antenna 7 (FIG. 5) and the power limiter 26 (not shown in FIG. 5) coupled between an output of the receiving antenna 7 and an input of the amplifier 25.

To extract a desired signal, the preamplifier/demodulator 9 (FIG. 5, 6) is comprised of a first and second band-pass filter 27, 28, a first and second clock rate amplifier 29, 30, a first, second, third and forth low-frequency phase detector 31, 32, 33, 34, a first and second low-frequency amplifier 35, 36, an adder 37 and a subtracter 38. An input of the first band-pass filter 27 is coupled to an output of the first phase detector 21, while its output is connected to an input of the first clock rate amplifier 29. An input of the second band-pass filter 28 is coupled to an output of the second phase detector 22, while its output is connected to an input of the second clock rate amplifier 30. An output of the first amplifier 29 is connected to signal inputs of the first and second low-frequency phase detectors 31, 32, and a signal output of the second amplifier 30 is connected to signal inputs of the third and forth low-frequency phase detectors 33, 34. A second output of the modulator 1 is connected to control inputs of the second and forth low-frequency phase detectors 32, 34, and a third control output of the modulator 1 is connected to control inputs of the first and third low-frequency phase detectors 31, 33. A phase of a control clock rate pulse sequence at the third output of the modulator 1 is shifted at a quarter period relative to that of the clock rate pulse sequence at the second output thereof. The outputs of the first and forth low-frequency phase detectors 31, 34 are connected to a first and second input of the subtracter 38, while the outputs of the second and third low-frequency phase detectors 32, 33 are connected with a first and second input of the adder 37. An output of the adder 37 is connected to an input of the first amplifier 35, and an output of the subtracter 38 is connected to an input of the second amplifier 36. Outputs of the first and second amplifiers 35, 36 are connected to the signal processing unit 10.

The apparatus (FIGS. 5, 6) operates in the following manner.

The modulator 1 generates four control pulse sequences at a clock rate F=1/T. An unipolar sequence having a duration Tt (an envelope curve in FIG. 7) is applied from a first output of the timing unit 17 to a control input of the first pulse modulator 11. An opposite-polar sequence of equal amplitude and a duration T/2 shifted at T/4 (FIGS. 11, 12) (an envelope curve in FIG. 7) is applied from a second and third output of the timing unit 17 to control inputs of the first, second, third and forth low-frequency phase detectors 31–34 in accordance with the diagram (FIGS. 5, 6), the sequence applied to control inputs of the first and third low-frequency phase detectors 31, 33 being T/4 ahead of the sequence applied to reference inputs of the second and forth low-frequency phase detectors 32, 34. An unipolar sequence having a duration Tt=Tr with a delay $\tau_{d1}=\tau_d+$Tr relative to the sequence applied to the control input of the first pulse modulator, is applied from the forth output of the timing unit 17 to the control input of the second pulse modulator 12 (an envelope curve in FIG. 8). The clock rate is selected in accordance with expression T=2Dmax/c, where Dmax is an ultimate distance to a search region boundary, c is a velocity of an electromagnetic wave propagation, Tt=2Dps/c, where Dps is a possible detection distance which can be always assessed by dimensions of the obstruction. The selected delay time $\tau_d$=2Dmin/c (FIGS. 7, 8) is determined by a dead region in the vicinity of the receiving antenna 7, required to eliminate a near signal from the obstruction and the operator. Dmin<Dps<Dmax. Tt<T.

Figure 7:
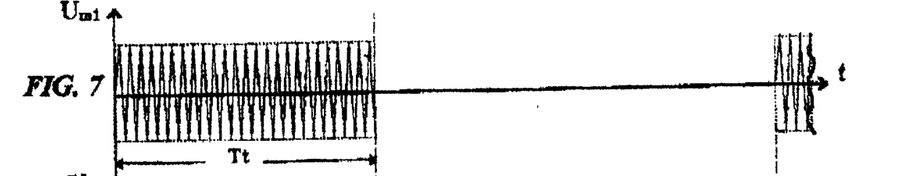
FIG. 7 is a timing diagram of the radiated RF signal at an output of a first pulse modulator in the transmitter.
Figure 8:
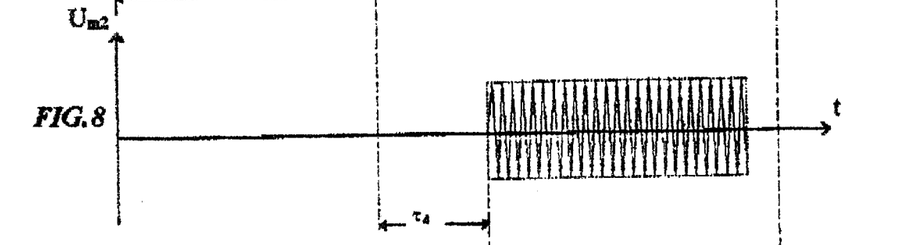
FIG. 8 is a timing diagram of an RF clock signal at an output of a second pulse modulator in the receiver.
Figure 9:
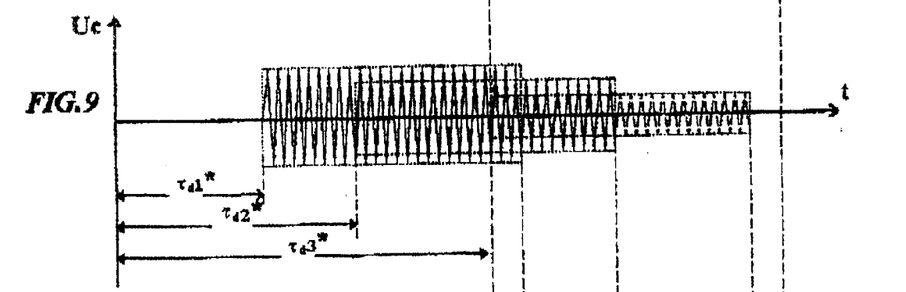
FIG. 9 is a timing diagram of received RF signals at an input of the microwave receiver.
Figure 10:
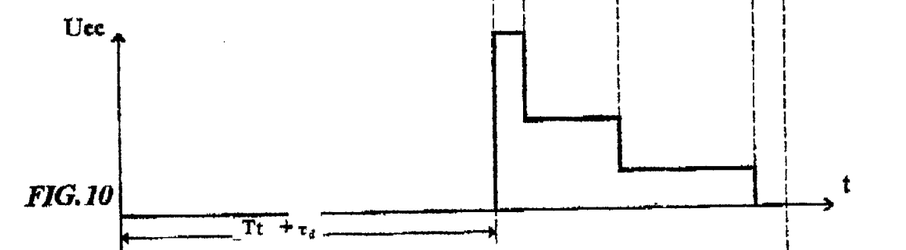
FIG. 10 is a timing diagram of a detected combined signal at outputs of a first and second phase detector in the microwave receiver.

The first sequence of the pulse time Tt is provided to the control input of the first pulse modulator 11 which opens a path in the transmitter 2 for the pulse time, so that an RF signal $U_{m1}$ is radiated (FIG. 7). RF signals Uc reflected from objects located at different distances (FIG. 9) arrive at the receiving antenna 7 (FIG. 5) or the receiving/transmitting antenna 15 (FIG. 6) at the input of the high-frequency amplifier 25. The amplified microwave signal is fed to the signal input of the in-phase power halving unit 24 in the microwave receiver 8. A heterodyne signal is provided to the signal input of the second pulse modulator from the second output of the power splitter 4. A radio frequency pulse $U_{m2}$ generated by the second pulse modulator 12 (FIG. 8) is fed to a signal input of the quadrature power halving unit 23. The in-phase power halving unit 24 and the quadrature power halving unit 23 both have a 90 degree phase shift between signals at their outputs. The pulse modulator 12, under the control of the second sequence with pulse time Tt of the timing unit 17, enables the local oscillator path after a time $\tau_{d1}$ equal to $\tau_d+$Tt upon the end of the radio frequency pulse $U_{m1}$ from the transmitter 2 path, diagram $U_{m2}$ (FIG. 8). In this case, a great portion of the reflected RF signal (FIG. 9) arriving from a near region with corresponding delays $\tau_{d1*}$, $\tau_{d2*}$ is not provided for subsequent processing, as shown in a simplified form in FIGS. 9 and 10. A waveform Ucc of the detected combined signal at the outputs of the first and second phase detectors 22, 23 looks approximately as depicted in FIG. 10. The diagram shows that the farther the object is located, the smaller the amplitude of the detected reflected signal, however, the greater its duration. This circumstance leads to narrowing of a dynamic range of energies of detected signals reflected from objects at different distances, since a duration of each signal and, hence, its energy defined as a product of the detected pulse power by its duration (area), is in direct proportion to the distance to the reflecting object. Based on the conventional radio location formula, it can be easily shown that this dynamic range is approximately the square root of the dynamic range obtained when a continuous or short-pulse sounding signal is used.

The dynamic range can be further narrowed by addition of the power limiter 26 for restricting the amplitude of pulse signals reflected from the objects located in the immediate vicinity of the receiving antenna 5 (or the receiving transmitting antenna 15) and by appropriate selection of the delay time $\tau_d$. The effect of the power limiter 26 on the signals reflected from the more distant objects will be quite negligible as the signals are greater in duration and smaller in amplitude. Therefore, the essential narrowing of the dynamic range of the received signals makes it possible to refuse from a considerable part of components associated with the signal compensation and its control in the receiving path, this resulting in improved sensitivity of the apparatus owing to the elimination of additional noise sources and the reduction in the time of locating an object.

To eliminate dead spots having a distance-dependent oscillating nature at the one-channel phase detection, an apparatus in a accordance with the invention can use a two-channel phase detection with reference (heterodyne) microwave signals that are 90° phase shifted. In this case, two band-pass filters: a first band-pass filter 27 and a second band-pass filter 28 (FIG. 5, 6), having a central modulated pulse repetition frequency F and a band required for a desired signal/noise ratio at the path output, are connected directly to signal low-frequency outputs of the first and second phase detectors 21,22 in the clock signal path. Amplitudes of sine waveforms of the pulse repetition frequency at the output of the first and second band-pass filters 27, 28 will be approximately in direct proportion to the area of the corresponding detected pulses. The signals are then amplified in the first and second clock rate amplifiers 29, 30 and provided in pairs to signal inputs of the first, second, third and forth low-frequency phase detectors 31–34.

Radio-frequency pulses provided to the signal inputs of the first and second phase detectors 21 and 22 from the output of the in-phase power halving unit 24 in the microwave receiver 8 can be represented as:

$u_c = Uc/2 \cos(wt + \Phi c)$, and radio-frequency pulses from the output of the quadrature power halving unit 23 can be represented as:

$u_{r1} = Ur/2 \cos(wt + \Phi r)$, $u_{r2} = Ur/2 \cos(wt + \Phi r + 90°) = -Ur/2 \sin(wt + \Phi r)$, where w is an RF signal carrier frequency, $\Phi c$, $\Phi r$ are initial phases, and Uc, Ur are pulse amplitudes, Inasmuch as in the first approximation the phase detectors are signal multipliers, at a time interval when envelope curves of the radio-frequency pulses in the local oscillator and receiver paths are overlapping, the first and second phase detectors 21 and 22 will output signals proportional to:

$u_1 \equiv \cos(wt + \Phi c) \cos(wt + \Phi r)$, $u_2 \equiv \cos(wt + \Phi c) \cos(wt + \Phi r + 90°)$, As the radio-frequency pulses are repeated at the repetition frequency F, after filtration in the band-pass filters 27, 28 and amplification in the amplifiers 29, 30, the latter will output sine clock signals:

$u_{y1} = Uy \cos(\Phi r - \Phi c) \cos(2 \pi Ft - \Phi y)$, $u_{y2} = Uy \sin(\Phi r - \Phi c) \cos(2 \pi Ft - \Phi y)$, where $\Phi y$ is a sum of phases of signal delays in the band-pass filters 27, 28 and the clock rate amplifiers 29,30, assuming their parameters equal in both channels, and a phase of a first harmonic of the clock frequency of the detected combined pulse signal having the Ucc waveform depicted in FIG. 10.

Figure 11:
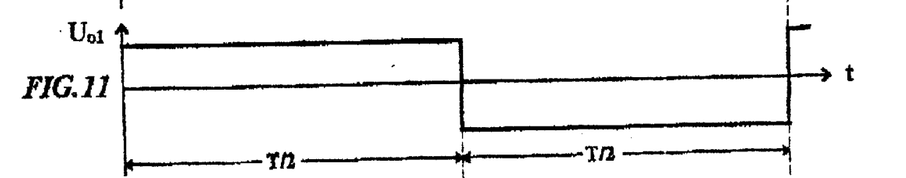
FIG. 11 is a timing diagram of syncs provided by a timing unit to a first and a third low-frequency phase detectors.
Figure 12:
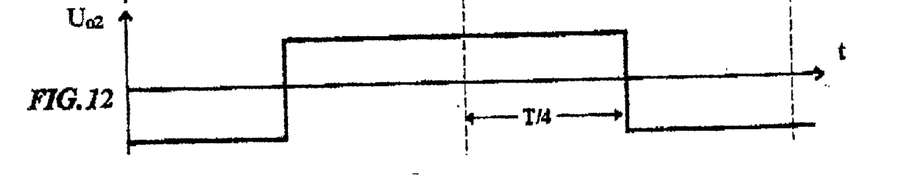
FIG. 12 is the same as FIG. 11 of syncs provided by a timing unit to a second and a forth low-frequency phase detectors.

From the outputs of the first and second amplifiers 29, 30, the signals are provided to the signal inputs of the low-frequency phase detectors 31–34: from the first amplifier 29 the signals are fed to the signal inputs of the first and second low-frequency phase detectors 31,32, and from the second amplifier 30 the signals are fed to the signal inputs of the third and forth low-frequency phase detectors 33, 34. Opposite-polar pulse sequences with the clock frequency F, which are illustrated in FIG. 11 and 12, are provided to the other, reference control inputs of the aforementioned low-frequency phase detectors from the second and third outputs of the timing unit 17. As the desired information in the sine waveforms $u_{y1}$ and $u_{y2}$ is contained in the modulated parameters Uy and $\Phi c$, and the clock frequency F substantially exceeds the upper frequency of the desired signal modulating the parameters, they are extracted in the low-frequency phase detectors 31–34 by multiplying the signals of the first clock frequency harmonics at the output of the amplifiers 29,30 and the reference signals at the output of the timing unit 17, followed by the low-frequency filtration thereof.

Representing the reference signals as:

$u_{o1} = Uo \cos(2 \pi Ft)$ at the control inputs of the second and forth low-frequency phase detectors 32, 34, and $u_{o1} = Uo \cos[2 \pi F(t - T/4)]$ at the control inputs of the first and third low-frequency phase detectors, obtain the following expressions for the signals at the outputs of the low-frequency phase detectors 31–34:

At the output of the first low-frequency phase detector 31:

$u_{d1} = kUy \cos(\Phi r - \Phi c) \cos(2 \pi Ft - \Phi y) Uo \cos(2 \pi Ft) =$
$= kUoUy \cos(\Phi r - \Phi c) \cos \Phi y$;

At the output of the second low-frequency phase detector 32:

$u_{d2} = kUy \cos(\Phi r - \Phi c) \cos(2 \pi Ft - \Phi y) Uo \cos[2 \pi F(t - T/4)] =$
$= kUoUy \cos(\Phi r - \Phi c) \sin \Phi y$;

At the output of the third low-frequency phase detector 33:

$u_{d3} = -kUy \sin(\Phi r - \Phi c) \cos(2 \pi Ft - \Phi y) Uo \cos(2 \pi Ft) =$
$= -kUoUy \sin(\Phi r - \Phi c) \cos \Phi y$;

At the output of the forth low-frequency phase detector 34:

$u_{d4} = -kUy \sin s(\Phi r - \Phi c) \cos(2 \pi Ft - \Phi y) Uo \cos[2 \pi F(t - T/4)] =$
$= -kUoUy \sin(\Phi r - \Phi c) \sin \Phi y$, where k is a conversion ratio of the low-frequency phase detectors.

The signals at the outputs of the low-frequency phase detectors 31–34 are described by different expressions, however, they can be transformed to two quadrature expressions by summing in the adder 37 the signals from the second and third low-frequency phase detectors 32,33, and subtracting the output signal of the forth low-frequency phase detector 34 from the output signal of the first low-frequency phase detector 31 in the subtracter 38. Using this procedure, after simple trigonometric transformation, the adder 37 will output:

$u_{d2} + u_{d3} = kUoUy \sin(\Phi c + \Phi y - \Phi r)$.

The subtracter 38 will output:

$u_{d1} - u_{d4} = kUoUy \cos(\Phi c + \Phi y - \Phi r)$.

The necessity of such processing is caused by the fact that the phase of the signal $\Phi c + \Phi y$, comprised of a random constant value associated with the distance to the object located and taking any values within the range $0 \ldots 2\pi + 2\pi n$ (n being an integer), and from a small modulated component, when added to the constant value $\Phi r$ may put the combined phase to a low tangential sensitivity region of the low-frequency phase detectors 31–34 in any of the channels. In this case, the sensitivity of the other channel will, on the contrary, increase since the channels are in the quadrature relationship, this enabling to extract information components of the signals Uy and $\Phi c$ in the subsequent quadrature processing.

Figure 5:
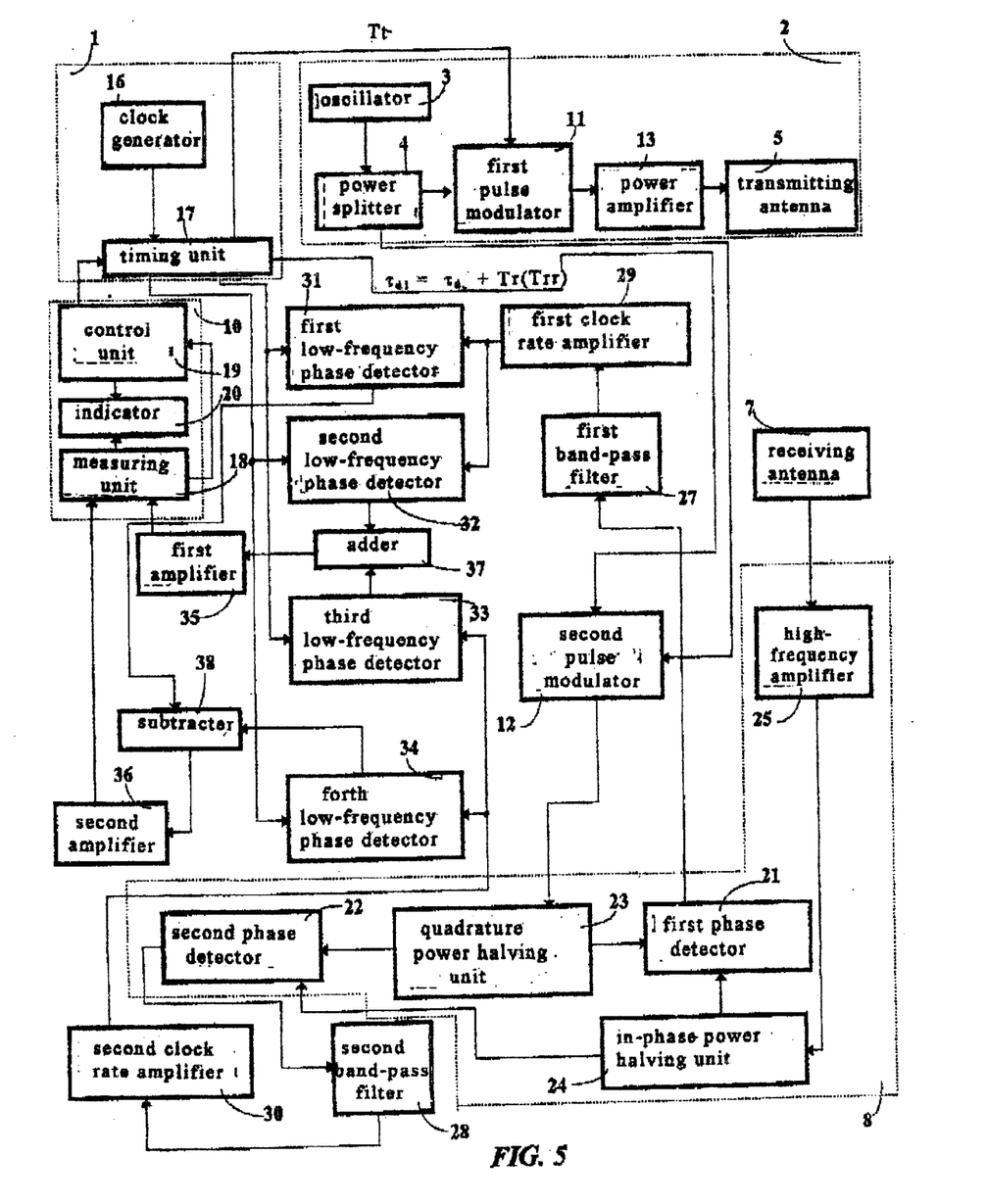
FIG. 5 is functional block diagram of a microwave locator with two-channel phase detection.

Output signals of the adder 37 and a subtracter 38, as shown in FIGS. 5, 6, are provided to inputs of similar first and second amplifiers 35 and 36, which suppress a constant non-informative component and amplify a variable component associated with the modulation of parameters Uy and $\Phi c$ by processes of human breath, heart beating and movements. Identical amplifiers 35,36 can be implemented in various circuits.

Figure 13:
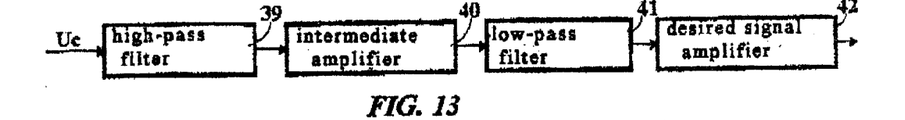
FIG. 13 is a functional block diagram of an amplifier mounted at an output of a subtracter or adder in the low-frequency phase detection unit.
Figure 14:
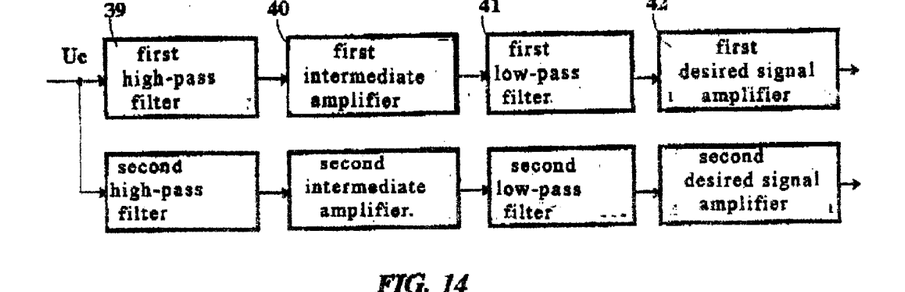
FIG. 14 is the same as FIG. 13 for a two-channel variant.
Figure 15:
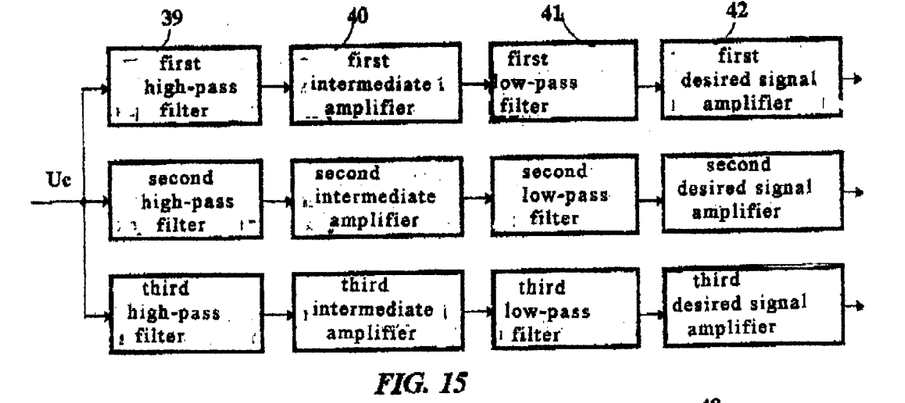
FIG. 15 is the same as FIG. 13 for a three-channel variant.

As an example, FIGS. 13 to 15 show embodiments of the amplifier 35 for apparatuses that do not require an extreme sensitivity. In such apparatuses, a minimum level of a desired signal amplified in the previous stages essentially exceeds 1/f noises of the amplifier per se, so that their effect can be neglected at low-frequency filtration. A single-channel embodiment (FIG. 13) can be used, in which a high-pass filter 39, an intermediary amplifier 40, a low-pass filter 41 and a desired signal amplifier 42 are connected in series. A filter 39 with a cutoff frequency corresponding to a minimal registered breath frequency (about 0.1 Hz) transmits only a variable signal component which is amplified in the intermediate amplifier 40. The filter 41 restricts the band of the processed signals to one of the highest harmonics of the heat beating signals or to an upper registered Doppler frequency associated with the object movements. In a two-channel embodiment (FIG. 14), only a breath signal is extracted in the first channel, all of the other signals being extracted in the second channel. Here, the cutoff frequency of the filter 41 is selected equal to the cutoff frequency of the filter 39 (0.6 . . . 0.7 Hz). The channel signals are provided for subsequent processing separately. In a three-channel embodiment (FIG. 15), frequency regions of human's breath, heart beating and movements are appropriately separated. The separation of the frequency region of the desired signal is justified both at subsequent analog processing to obtain the maximum information possible of the object, and at digital processing to align the signal dynamic ranges in the channels by selection of different gains in them, this enabling to restrict bit capacity of the analog-to-digit converter in the digital system. For the apparatuses with increased sensitivity it is required to introduce an additional signal modulation at a frequency lying outside the region of 1/f noises and to provide compensation at this frequency. In this case, the amplifier 35 circuit will be more sophisticated.

The filtered signals from outputs of the first and second amplifiers 35, 36 are provided to the signal processing unit 10 for further processing. The processing may be accomplished both by analog means, and a digital processor after the analog-to-digital conversion. This processing results in extracting and measuring parameters of an information (variable) component of the signal, associated with fluctuations in the radio location target owing to human's breath, heart beating or movements. The signal processing unit 10 can be also implemented in various circuits.

Figure 16:
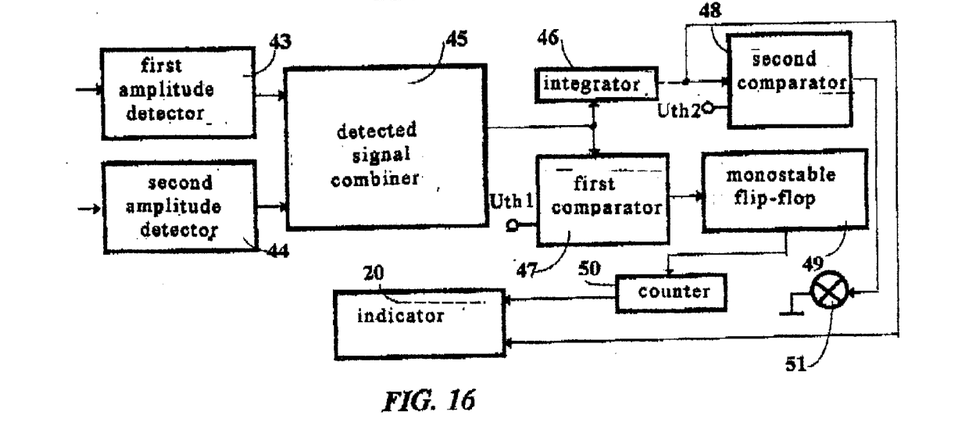
FIG. 16 is a functional block diagram of a measuring unit.

By way of example, quadrature signals at the channel outputs of the first and second amplifiers 35, 36 can be detected by amplitude detectors 43, 44 (FIG. 16). The signals are then combined in the detected signal combiner 45, and the combined signal is provided to inputs of an integrator 46 and a first comparator 47. An output of the integrator 46 is connected to an input of a second comparator 48. The first comparator 47 generates trigger pulses for a monostable flip-flop 49 each time when the combined signal exceeds a level Uth1. The monostable flip-flop 49 generates pulses of equal duration, the frequency of which is measured by a counter 50 and can be displayed on the indicator 20. A signal accumulated in the integrator 46 is provided to the second comparator 48 which compares the accumulated level with a threshold voltage Uth2 during some predetermined time. When the threshold is exceeded within the predetermined time, the second comparator 48 outputs a signal to an alarm 51. Upon expiration of the predetermined time, the integrator is reset, and the process is repeated. The signal levels in all of the channels can be monitored on the indicator 20. A similar processing unit is used for each channel in the first and second amplifiers 35, 36.

As the above-described circuit is rather sophisticated, it would be reasonable to employ digital processing. In the case of digital processing (not shown), the signal processing unit 10 should have an analog-to-digital converter, a processor and the indicator 20 in the form of a display. In this case, conventional functional circuits and processing techniques are employed. The use is made of a digital narrow-band filtration, a spectral analysis on the basis of a Fourier transform unit with appropriate displaying of the processing result.

Parameters of the microwave locator are controlled by the control unit 19 so that to establish a search zone for fast survey of a maximum space, to eliminate interference and to determine a distance to the detected object. In the case of digital signal processing, this function can be combined with control function in a single apparatus, a computer.

By modifying the time Tt in operation, a distance to the object detected can be also measured by a reduction or loss of a signal therefrom when Tt is reduced. Here, to provide a time separation between the radiation, delay and reception processes, the relation T/Tt>2 should be maintained. To reduce interference introduced by distant objects, this ratio should be as large as possible. However, with the increase in the ratio, off-duty factor of the received pulses raises, the latter leading to aggravation in the apparatus sensitivity, therefore, the parameter T should be set in accordance with the specific tasks set.

INDUSTRIAL APPLICABILITY

The method for locating a living object and the microwave locator in accordance with the present invention can be most successfully employed in technical means for search and rescue services for objectively detecting the presence of a human with life signs under obstructions.

What is claimed is:

1. A method for locating a living object, including radiating a radio frequency (RF) signal, receiving a reflected RF signal, detecting a component of the received RF signal, wherein the received RF signal has been modulated in amplitude and phase corresponding to a heart rate or breath frequency of a substantially motionless living object, and establishing, on the basis of the detected component, the presence of a living object, wherein said radiating of an RF signal is provided within a fixed time Tt, said receiving of a reflected RF signal is provided within a fixed time Tr equal in duration to the fixed time Tt of the radiated RF signal plus a delay $\tau_d$ between an end of the RF signal radiation and a beginning of the reflected RF signal reception, the method further comprising:
measuring, once the modulated component is detected, a level of the modulated component;
modifying the reception time of the reflected RF signal until the level of the modulated component decreases relative to the level of the modulated component in the reflected RF signal received within the fixed time Tt, and up to an end of arrival of the reflected RF signal; and
determining a distance to a living object location by the following expression:

$$D = c(\tau_d + Trr)/2$$

where c is a velocity of propagation of an RF signal,
$\tau_d$ is a duration of a delay between the end of radiation and the beginning of reception of the RF signal, and Trr is a time of reception of the reflected RF signal, within which the level of the modulated component level has been decreased, said time corresponding to a period from the beginning of the reflected RF signal reception to the end of the reflected RF signal arrival.

2. A method as set forth in claim 1, wherein when the modulated component is detected, the reflected RF signal reception time is reduced in equal intervals.

3. A method as set forth in claim 1, wherein when the modulated component is detected, the reflected RF signal reception time is modified using a successive approximation technique.

4. A method as set forth in claim 1, wherein the RF signal is radiated at a frequency determined as $$f(GHz)=15[0.23-\alpha d+\sqrt{(0.23-ad)^{2+0.1}}],$$

where $\alpha = tg\ \delta\sqrt{\in}$ is an attenuation ratio, $tg\delta$ and $\in$ being a dielectric loss tangent and an effective portion of a relative dielectric constant of an obstruction, respectively, at a frequency of 1 GHz, and d is an assumed maximum obstruction thickness, [m].

5. A microwave locator comprising a modulator and a transmitter including an oscillator, a power splitter and a transmitting antenna, all having signal inputs connected in series to signal outputs to radiate an RF signal with modulation, a receiver including a receiving antenna, a microwave receiver, a preamplifier/demodulator and a signal processing unit, all having signal outputs connected in series to signal inputs to receive a reflected RF signal having a component modulated by a living object heart rate or breath, and to extract the component at an output of the preamplifier/demodulator, a second signal output of the power splitter being connected to a control input of the microwave receiver, a first control output of the modulator being connected to the transmitter, and a second and a third outputs of the modulator being connected to a first and a second control inputs of the preamplifier/demodulator, respectively, wherein said modulator modifies a duration of control pulses and locks them, said microwave locator further comprising a first pulse modulator in the transmitter and a second pulse modulator in the microwave receiver, a first signal output of the power splitter being connected to an input of the transmitting antenna via a signal input and a signal output of the first pulse modulator, and a second signal output of the power splitter being connected to a control input of the microwave receiver via a signal input and a signal output of a second pulse modulator, a control input of a first pulse modulator being connected to a first control output of the modulator to lock the radiation time of the RF signal, the modulator having a forth control output connected to a control input of the second pulse modulator to receive the reflected RF signal in the receiver with a delay relative to an end of the RF signal radiation by the transmitter and to modify an enable time of the microwave receiver, whereby the signal processing unit measures the modulated component level.

6. A microwave locator as set forth in claim 5, wherein said microwave receiver uses two-channel quadrature phase detection.

7. A microwave locator as set forth in claim 6, wherein said microwave receiver comprises a first and second phase detector, a quadrature power halving unit, an in-phase power halving unit having a signal input connected to an output of the receiving antenna, a first output connected to a first input of the first phase detector, and a second output connected to a first input of the second phase detector, an output of the second pulse modulator is connected to an input of the quadrature halving unit, said input being the control input of the microwave receiver, a first output of the quadrature halving unit is connected to a second input of the first phase detector, and a second output thereof is connected to a second input of the second phase detector.

8. A microwave locator as set forth in claim 7, wherein said microwave receiver further includes a high-frequency amplifier, a signal input of the in-phase halving unit being connected to an output of the receiving antenna via the high-frequency amplifier.

9. A microwave locator as set forth in claim 8, wherein said microwave receiver further includes a power limiter, a signal input of the high-frequency amplifier being connected to the output of the receiving antenna via a signal output and a signal input of the power limiter.

10. A microwave locator as set forth in claim 7, wherein said preamplifier/demodulator is comprised of a first and second band-pass filter, a first and second clock rate amplifier, a first, second, third and forth low-frequency phase detector, a first and second amplifier, an adder and a subtracter, a signal input of the first band-pass filter being coupled to a signal output of the first phase detector, and a signal output of the first band-pass filter being connected to a signal input of the first clock rate amplifier, a signal input of the second band-pass filter being connected to a signal output of the second phase detector, a signal output of the second band-pass filter being connected to a signal input of the second clock rate amplifier, a signal output of the first clock rate amplifier being connected to signal inputs of the first and second low-frequency phase detectors, and a signal output of the second clock rate amplifier being connected to signal inputs of the third and forth low-frequency phase detectors, a second output of the modulator being connected to control inputs of the second and forth low-frequency phase detectors, and a third control output of the modulator being connected to control inputs of the first and third low-frequency phase detectors, wherein a phase of a control clock rate pulse sequence at the third output of the modulator is shifted at a quarter period relative to that of a clock rate pulse sequence at the second output thereof, outputs of the first and forth low-frequency phase detectors are connected to a first and second input of the subtracter, outputs of the second and third low-frequency phase detectors are connected to a first and second input of the adder, an output of the adder is connected to an input of the first amplifier, and an output of the subtracter is connected to an input of the second amplifier, outputs of the first and second amplifiers being connected to the signal processing unit.

11. A microwave locator as set forth in claim 10, wherein said first and second amplifiers are circuits comprised of a high-pass filter, an intermediary amplifier, a low-pass filter and a signal amplifier, all connected in series.

12. A microwave locator as set forth in claim 11, wherein each of said first and second amplifiers is multi-channel, one channel being used to extract a modulated component corresponding to a living object's breath, a second channel being used to extract a modulated component corresponding to a living object's heart, and a third channel being used to extract a modulated component corresponding to living object's movements.

13. A microwave locator as set forth in claim 10, wherein said measurement unit in the signal processing unit includes a first and second amplitude detector, a detected signal combiner, an integrator and a first and second comparator, a monostable flip-flop, a counter and an alarm, a signal input of the first amplitude detector being connected to a signal output of the first amplifier, a signal input of the second amplitude detector being connected to a signal output of the second amplifier, outputs of the first and second amplitude detectors being connected to a first and second input of the detected signal combiner, respectively, an output of the detected signal combiner being connected to a signal input of the integrator and a signal input of the first comparator, a second input of the comparator being a threshold input, a signal output of the integrator being connected to a signal input of the second comparator, another input of the second comparator being a threshold input, while an output thereof is connected to the alarm, the signal output of the integrator being further connected to a first input of the indicator in the signal processing unit, a signal output of the first comparator being connected to a signal input of the monostable flip-flop having a signal output connected to the counter, and an output of the counter being connected to a second input of the indicator.

14. A microwave locator as set forth in claim 5, wherein said transmitter further includes a power amplifier, a signal output of the first pulse modulator being connected to an input of the transmitting antenna via a signal input and output of the power amplifier.

15. A microwave locator as set forth in claim 5, further comprising a circulator, wherein the transmitting antenna and the receiving antenna form a single receiving/transmitting antenna, the first pulse modulator being connected to the receiving/transmitting antenna via a first branch of the circulator and a second branch thereof in circulation direction, the microwave receiver being coupled to the receiving/transmitting antenna via the second and a third branch of the circulator in the circulation direction.

16. A microwave locator as set forth in claim 5, wherein said modulator is comprised of a clock generator and a timing unit having a clock input connected to an output of the clock generator, outputs of the timing unit being a first, second, third and forth output, respectively, of the modulator, the signal processing unit including a measurement unit, a control unit and an indicator, wherein an input of the measurement unit is an input of the signal processing unit, a control output of the measurement unit is connected to an input of the control unit, and a signal output thereof is connected to a signal input of the indicator, a first control output of the control unit is connected to a control input of the timing unit, and a second control output of the control unit is connected to a control input of the indicator.

\* \* \* \* \*